US011129561B2

(12) United States Patent
Abramov et al.

(10) Patent No.: US 11,129,561 B2
(45) Date of Patent: Sep. 28, 2021

(54) MODULAR DEVICE AND METHOD FOR ANALOG ELECTROENCEPHALOGRAPHY SYNCHRONIZATION WITH OSCILLATING ELECTRICAL LIGHT-RELATED EVENTS, AND MOTOR BEHAVIORS

(71) Applicant: FUNDAÇÃO OSWALDO CRUZ (FIOCRUZ), Rio de Janeiro (BR)

(72) Inventors: Dimitri Marques Abramov, Rio de Janeiro (BR); Paulo Ricardo Galhanone, Rio de Janeiro (BR); Marcos Antonio Dias Lima, Rio de Janeiro (BR); Carlos Henrique Quintanilha Martins, Rio de Janeiro (BR)

(73) Assignee: FUNDAÇÃO OSWALDO CRUZ (FIOCRUZ), Rio de Janeiro (BR)

( * ) Notice: Subject to any disclaimer, the term of this patent is extended or adjusted under 35 U.S.C. 154(b) by 354 days.

(21) Appl. No.: 16/085,775

(22) PCT Filed: Mar. 17, 2017

(86) PCT No.: PCT/BR2017/050062
§ 371 (c)(1),
(2) Date: Sep. 17, 2018

(87) PCT Pub. No.: WO2017/156613
PCT Pub. Date: Sep. 21, 2017

(65) Prior Publication Data
US 2019/0104960 A1   Apr. 11, 2019

(30) Foreign Application Priority Data
Mar. 18, 2016 (BR) .......................... 102016006010-9

(51) Int. Cl.
*A61B 5/0484* (2006.01)
*A61B 5/05* (2021.01)
(Continued)

(52) U.S. Cl.
CPC ................ *A61B 5/377* (2021.01); *A61B 5/05* (2013.01); *A61B 5/16* (2013.01); *A61B 5/378* (2021.01);
(Continued)

(58) Field of Classification Search
CPC ........ A61B 2560/0242; A61B 5/04842; A61B 5/0484; A61B 5/04845; A61B 5/16;
(Continued)

(56) References Cited

U.S. PATENT DOCUMENTS 4,013,068 A * 3/1977 Settle ................... A61B 5/0476
600/545
4,913,160 A 4/1990 John
(Continued)

*Primary Examiner* — Christine H Matthews
*Assistant Examiner* — Joshua Daryl D Lannu
(74) *Attorney, Agent, or Firm* — Knobbe, Martens, Olson & Bear, LLP

(57) ABSTRACT

This invention relates to a device that is intended to synchronize electroencephalograms (EEGs), recorded by any digital equipment, to physical events (sensorial, visual or auditory stimuli) and behavioral events (motor response, vocal response), in order to allow EEG signal mediation for the purpose of visualizing Evoked Potentials or Event-Related Potentials, which are important research subjects in the neurosciences and clinical investigations into neurological and psychiatric pathologies. This invention allows any digital EEG device to be transformed into equipment that can record Evoked Potentials. This invention also provides a method for analog synchronization of EEGs with oscillating electric light-related events and motor behaviors.

10 Claims, 8 Drawing Sheets

(51) Int. Cl.
*A61B 5/16* (2006.01)
*A61B 5/377* (2021.01)
*G16Z 99/00* (2019.01)
*A61B 5/00* (2006.01)
*A61B 5/38* (2021.01)
*A61B 5/378* (2021.01)
*A61B 5/0531* (2021.01)
*A61B 5/11* (2006.01)
*G16H 20/70* (2018.01)

(52) U.S. Cl.
CPC .............. *A61B 5/38* (2021.01); *A61B 5/7282* (2013.01); *G16Z 99/00* (2019.02); *A61B 5/0531* (2013.01); *A61B 5/11* (2013.01); *A61B 5/7225* (2013.01); *A61B 2560/0242* (2013.01); *G16H 20/70* (2018.01)

(58) Field of Classification Search
CPC ....... A61B 5/05; A61B 5/0531; A61B 5/7282; A61B 5/11; A61B 5/7225; G16Z 99/00; G16H 40/63; G16H 20/70
See application file for complete search history.

(56) References Cited

U.S. PATENT DOCUMENTS

| | | |
|---|---|---|
| 7,384,399 B2 | 6/2008 | Ghajar |
| 8,938,289 B2 | 1/2015 | Einav et al. |
| 2005/0177065 A1* | 8/2005 | Ghajar .................. A61B 3/113 600/558 |
| 2010/0145215 A1 | 6/2010 | Pradeep et al. |
| 2015/0126802 A1 | 5/2015 | Lim et al. |

* cited by examiner

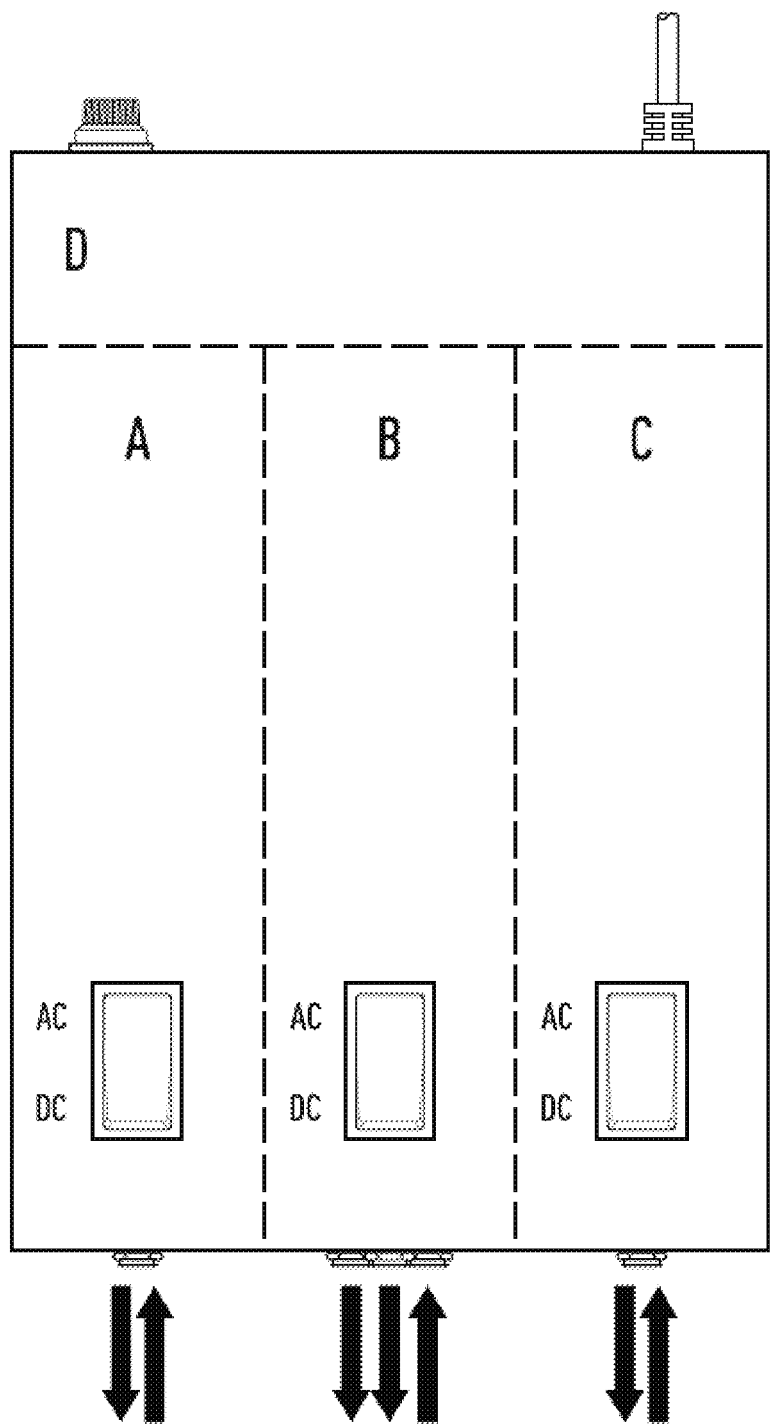
FIGURE 2.1

FIGURE 2.2
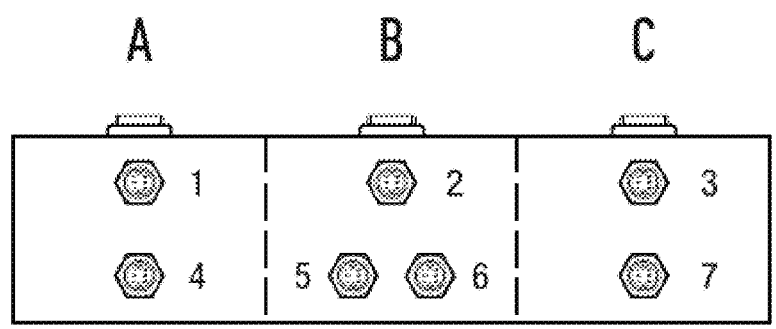
FIGURE 2.3
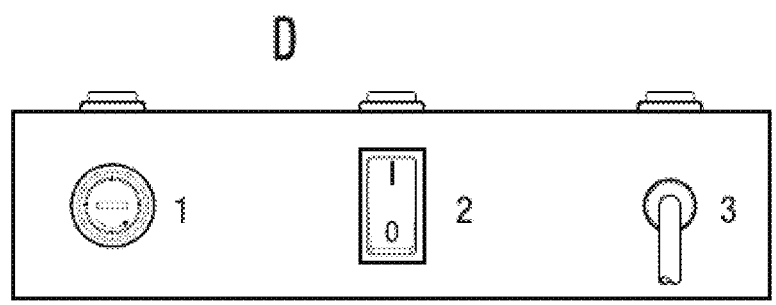

MODULAR DEVICE AND METHOD FOR ANALOG ELECTROENCEPHALOGRAPHY SYNCHRONIZATION WITH OSCILLATING ELECTRICAL LIGHT-RELATED EVENTS, AND MOTOR BEHAVIORS

BACKGROUND

Field

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The device constituting this invention is intended to synchronize electroencephalograms (EEGs), recorded by any digital equipment, with physical events (sensorial, visual or auditory stimuli) and behavioral events (motor response, vocal response), thus allowing EEG signal mediation for the purpose of visualizing Evoked Potentials or Event-Related Potentials, which are important research subjects in the neurosciences and clinical investigations into neurological and psychiatric pathologies. This invention allows any digital EEG device to be transformed into equipment that can record Evoked Potentials. The invention also provides a method for the analog synchronization of EEGs with oscillating electric light-related events and motor behaviors.

Description of Related Art

Evoked Potentials (PE) are electrophysiological responses evoked from the nervous system by a variety of events, such as endogenous cognitive processes or sensorial stimuli synchronized with a behavioral response. There are currently two alternative methodologies for materializing Evoked Potentials:

using dedicated equipment for materializing Evoked Potentials (such as that made by the Nicolet®, Nihon Kohden® and Neurotec® manufacturers, for example). Despite the high quality of the tests that they produce, they are systems designed to provide medical care and with few stimulation protocols, hampering the customization of tests. Consequently, such equipment is of little use for research purposes. These items of equipment are extremely expensive (they are more costly than the electroencephalogram equipment made by the same manufacturers) and have few channels (average of four). Equipment prices rise steeply for more channels.

Methodologies using digital electroencephalography equipment linked to computer systems, such as the following, for example:

Pscychotoolbox-MatLab®, CORTEX® and Presentation®. These computer systems produce stimulation protocols for obtaining Evoked Potentials, in parallel to a programmable trigger, synchronized with the events in these protocols, which is sent to the EEG equipment through an outlet port on the computer. These systems are feasible only for scientific research, for the following reasons: high complexity of these systems (for their installation, maintenance, operation and programming) which normally require a technician with professional qualifications, found only in laboratories with ample expertise; possibility of synchronization errors resulting from programming mistakes or even computer problems intrinsic to extremely complex operating systems (such as Windows®) that might adversely affect the accurate timing of software-hardware-EEG interactions. All these variables undermine the feasibility of using this methodology for medical care.

There is a need at the state of the art for the development of a definitive and innovative conceptual technology that can handle the materialization of Neurophysiology Event Protocols (Evoked Potentials) and ensuring: accurate synchronization of events and signals; procedures that are easy to perform; low costs; and universal access to Evoked Potential tests by countless electroencephalography units already in place or to be implemented

SUMMARY

This purpose of this invention is to provide accurate marking of stimuli presentation instants and responses to these stimuli in Neuroscience and Evoked Potentials research protocols for clinical neurophysiology, with no need for computer systems equipped with stimulation management applications.

This invention proposes a method and a method and a device that allows synchronization between sensorial stimuli and an electroencephalogram (EEG) in order to obtain Evoked Potentials.

The device resulting from this invention allows Event-Related Potentials (Evoked Potentials) to be obtained through using ordinary EEG equipment, through the transduction of the events submitted to the subject (or behavioral events) in an analog signal that synchronizes these events with the encephalographic recording, generating trustworthy latencies in the evoked potential wave.

The device resulting from this invention allows synchronization of the electroencephalogram (EEG) recorded by any digital equipment or through analog-digital conversion with events: (1) light, emitted by any source, such as the sun, liquid-crystal display (LCD), cathode-ray tube (CRT), cinematographic projections, all types of lamps and all types of light-emitting diodes (LEDs), in any color (wavelength) within the visible spectrum and at any intensity; (2) electrical oscillations at any frequency, voltage and current, deriving from (2.a) from the outlet of an analog or digital electronic sound source (electric signal outlet to loudspeakers, earphones or amplifiers, either monophonic or stereophonic); (2.b) from a transduction device for another physical event into an electrical event (transducer of voltage, vibration, sound, pressure, temperature, humidity, flow or any biological events); (2.c.) From an electric signal conditioning device (amplifiers or transformers), (2.d) from a skin impedance measurement device, with or without reproduction of the respective electric signal to a parallel outlet; and (3) behavioral motor responses produced actively in all four limbs, either individually or in pairs, through activating switch devices; producing square electrical envelopment waves (i.e., triggers) whose lengths vary in order to demarcate the event in time, transmitting these triggers to the EEG equipment through its DC channels (at voltages between −5V and +5V) or AC (for example, −50 mV a +50 mV), that are recorded on the electroencephalogram concomitantly with the biological signal.

Through the device constituting this invention, it is possible to produce EEG signal mediation for the purpose of visualizing Evoked Potentials or Event-Related Potentials, after the recording thereof, as a subject for neuroscience research and clinical investigations of neurological and psychiatric pathologies. This invention allows any digital EEG device to be transformed into equipment that can record Evoked Potentials.

Among the advantages of this invention, we may mention:

with markings taken directly from the presented stimuli and the responses generated by patients, delays are fixed and known, defined only by the electronic signal spread times, which can thus be easily offset through software during the post-analysis stage;

with the analog generation circuit of the trigger, the signal is already defined by being introduced directly into the DC or even AC channels;

any digital EEG equipment may be used as off-line Evoked Potentials (ERP) equipment, which could make the use of medium and long latency Evoked Potentials more popular in neurological clinical practice, disseminating a low-cost safety technology for functional research into the nervous system (useful for monitoring patients with demyelinating diseases and diagnoses of visual tract lesions, for example); and, stimuli management applications are not required. Any software or even a sequence of stimuli recorded in a media file may be used for stimulation This invention proposes a novel functional concept that lies in the analog synchronization of EEG signals with physical and behavioral events in order to obtain Evoked Potentials through a device linked to the EEG and external to this unit.

The device presented here exemplifies the implementation of the invention in question, as it allows Event-Related Potentials (Evoked Potentials) to be obtained through using ordinary digital EEG equipment by electronic manipulation of the events submitted to the subject (light stimuli transduced by photocell, or electrical oscillations deriving from sound equipment outlets, the transduction of other physical events, conditioning, biological signals or skin impedance measurements related to such events or behavioral events (motor responses of the upper and/or lower limbs) in an analog signal that synchronizes these events with the encephalographic recording, for easier examination of the exact evoked potential wave latencies, as the trigger markings are directly derived from analog processing of the presented stimuli and the responses generated by the patients. The delays inherent to analog processing time are set and known, defined only by the electronic signals spread time, which can thus be easily offset through software in the post-analysis stage. With the analog generation circuit of the trigger, the signal is already defined by being introduced directly into the DC or even AC channels. This means that any digital EEG equipment may be used for off-line processing of evoked potentials. As digital EEG equipment has a relatively low analog-digital conversion time (1000 points per second or less), only medium and long latency evoked potentials (greater than 50 ms) can be analyzed safely with this conventional equipment. We note that this methodology will be appropriate for detecting visual, medium-latency auditory and cognitive evoked potentials (endogenous, related to the motor responses), thus disseminating a safe and low-cost functional technology for examining the central nervous system during research activities as well as medical care (where it is very useful for monitoring patients with demyelinating diseases, visual system alterations evaluations and studies of the progression of cognitive diseases, for example); there is no need for very expensive dedicated equipment and computer systems with stimuli management applications. Any software may be used for stimulation or even a sequence of stimuli recorded in a media file.

BRIEF DESCRIPTION OF THE DRAWINGS

FIGS. 2.1, 2.2 and 2.3 offer a schematic view of the necessary elements in the top and back panels of the standard device addressed by the invention, schematized with dashed lines showing the functional divisions of the system into modules.

DETAILED DESCRIPTION

The basic elements of the device addressed by the invention are presented below.

The device constituting the invention is a modular item of equipment, with three types of function modules: a motor response processing module (A, as shown in FIG. 2.1); electrical oscillation processing module (B, as shown in FIG. 2.1); and the light processing module (C, as shown in FIG. 2.1). Module D is the power feed and control module, containing the power switches, the power input and the voltage safety control (fuse), that distributes electricity to all three (or more) function modules.

A unit of the device constituting the invention may contain as many function modules as wished, in a customized manner. For example, two modules B, one module A and two modules C. As modules A and B have two input channels each, generating trigger waves at the outlet in a single channel, with different amplitude levels, which can indicate whether there was a response or the presence of a stimulus in one, the other or both module input channels.

In order to demonstrate the operations of this invention, a unit was set up for the device (described here) with three function modules (with 5 input channels and three output channels that together produce five individual response patterns), in the belief that much of the demand will be met with this configuration. Nevertheless, other configurations may be set up through arraying the function modules side-by-side on a single level (keeping the thickness of the device), with a single circuit board. Further explanations are presented in greater detail in the references for the Figures.

Figure 1A:
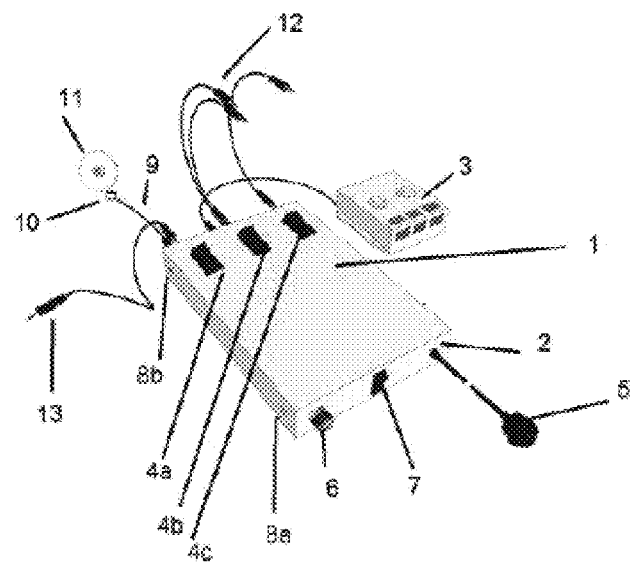
FIGS. 1A and 1B offer a general schematic overview of the device constituting the invention in a preferred embodiment.
Figure 1B:
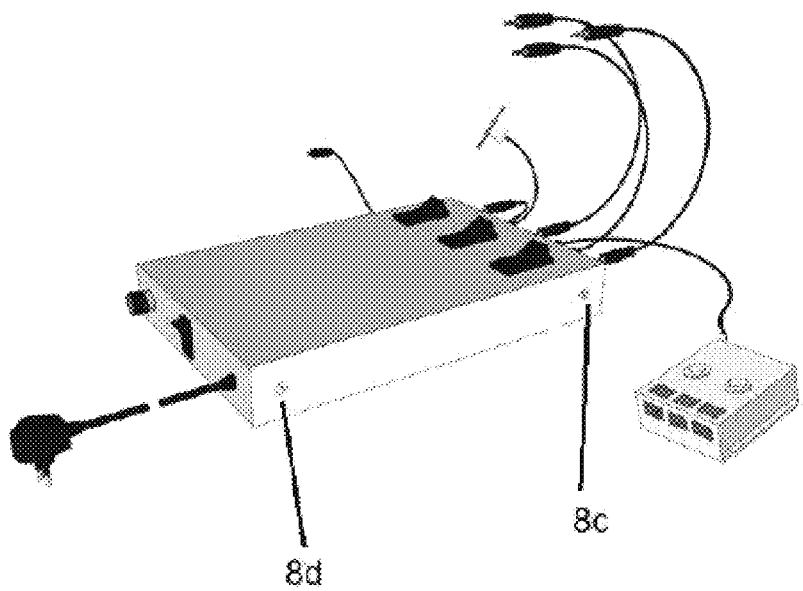

The numerical references in FIGS. 1A-1B correspond to a unit of the device constituting the invention with three modules, one of each type: A, B and C. Representing a preferred mode of the invention, FIGS. 1A-1B present the following structural elements:

(1) Housing Lid: sheet made from metal or plastic material forming the top and sides of the outer housing of the device, with top openings for the 4a-c switches.

(2) Housing Body: composed of the outer front, back and lower parts of the housing with all the plugs and outlets of the device, and holding its circuit board. There are screws on the side of the body to hold the housing lid in place. There is a crossbar on the housing body along the length of the device, fixed to its sides, where the 4a-c selection switches are attached.

(3) Button Unit: composed of two buttons for entering motor responses.

(4) a-c switches that select voltage levels at the outlets for each outlook function module (a—motor response module; b—electrical oscillations module; and c—light detection module). If DC is selected, the output voltage varies between −5V and +5V (for entering the DC channels of the EEG equipment). Is AC is selected, the output voltage varies between −50 and +50 mV (for the AC channels of the EEG equipment, or for entering the EEG channel).

(5) Power Source: the device uses a regular power source with a switch, with an inflow of alternating current at 100-240V, 50-60 Hz, and an outflow of continuous current at no more than 12V and 1000 mA.

(6) Threaded fuse port (7) Power switch.

(8) Screws a-d: for attaching the lid of the device to its body (9) Photocell input cable

(10) Suction cup: the photocell is attached to a smooth surface (an LCD or CRT screen, for example) by a suction cup. When necessary, this allows the photocell to be attached to any other type of surface by any other means whatsoever, such as adhesive tape.

(11) Photocell: on the device, we use a broad-spectrum visible light energy uptake current-breaking photocell.

(12) Function module trigger output tables: these are the cables connecting to the DC and AC channels on the EEG equipment. The standard outlets on the embodied device are P1 mono type. Many types of equipment use different connectors (such as RCA); in this case, adapters (rabichos) that are found easily on the market would be needed to use the device constituting the invention.

(13) Electrical oscillations input table: set up with a stereo P2 connector, in order to link directly into an audio outlet (speaker out) on many different types of equipment, ranging from computers to television sets, mp3 and DVD players, as the use of this module to synchronize sound stimuli will be the rule. In order to connect other devices, adapters may be needed or even signal adjusters (for electrical oscillations coming from sensors or other measurement devices/biological examinations).

FIG. 2.1 shows a schematic view of the top panel of the device addressed by the invention. The dashed lines represent imaginary divisions of the four modules constituting the preferred configuration, with three function modules (A: motor response module, B: electrical oscillations module, C: light detection module), and the power feed module (D), which constitutes the entire front part of the device, as shown in FIG. 1. It is noted that the switches (corresponding to Switches 4a-c in FIG. 01) of the respective modules define the output voltage range for each module: in the AC position, the voltage range is compatible with the standards for digital EEG devices (no more than 50 mV to +50 mV), and for the DC position, the voltage range is −5 a +5V. The arrows represent the number of inlets and outlets for each function module.

FIG. 2.2 shows a rear view of the device in a preferred embodiment (see FIG. 2.1), containing the device signal inlets and outlets. All outlets are square waves with durations identical to the input signal, with ranges depending on whether they are intended for a DC or AC channel (defined by the position of Selector Switches 4a to c). Specifically, the elements in the Figure are:

(1) Behavioral response inlet: two single-reference channels that are connected to the button unit (see FIG. 3) by a stereo connector (2 phases, 1 neutral).

(2) Electrical oscillations inlet: two single-reference input channels with a stereo connector (2 phases, 1 neutral), that detects oscillations at less than 100 Hz as individual events, and oscillations at more than 100 Hz at a frequency compatible with most soundwaves, as a single event.

(3) Photocell inlet (4) Motor response module trigger outlet: Pressing Button 1 (channel 1) produces a positive wave of +3V (+30 mV if the AC option is selected on corresponding Switch 4—see FIG. 1); pressing Button 2 (channel 2) produces a positive wave of +2V (+20 mV if the AC option is selected); while pressing both buttons simultaneously produces a positive wave of +5V (+50 mV if the AC option is selected)

(5) Electrical oscillation module trigger outlet: detecting electrical oscillations events produces 2, 3 or 5V waves (20, 30 or 50 mV for the respective AC options), for either the right, the left or both input channels during the event, which has a set response latency (measured between the peak of the first oscillation and maximum trigger voltage) of 4 mseg (four oscillations lasting 10 mseg or more), or 3 mseg (four oscillations lasting less than 10 mseg).

(6) Electrical oscillation outlet: a female stereo connector that reproduces the respective input signal from both channels. This is useful for signal sharing with another device or to activate a speaker (loudspeakers, earphones, etc).

(7) Light module trigger outlet: the light module produces a 5V trigger wave (50 mV for the AC option), with latency set for a maximum voltage of 2 mseg. On the threshold of inactivity, the maximum detection frequency for light pulses is 30 Hz or more. For the xenon lamp flashes (color 6500 K, 30 $cd/m^2/W$, pulse duration: 20 ps), the maximum detection frequency is 60 Hz or more. For an LCD or CRT display operating at 60 Hz (our standard), the maximum stimulation frequency is 30 Hz (one light cycle, one dark cycle). See FIG. 8.

FIG. 2.3 provides a front view of the back of the device in a preferred embodiment, which has the controls and the module D input. Specifically, the elements in this Figure are:

(1) Threaded fuse port.

(2) Power switch.

(3) Power cable input: from the power source. (see FIG. 1)

Figure 3:
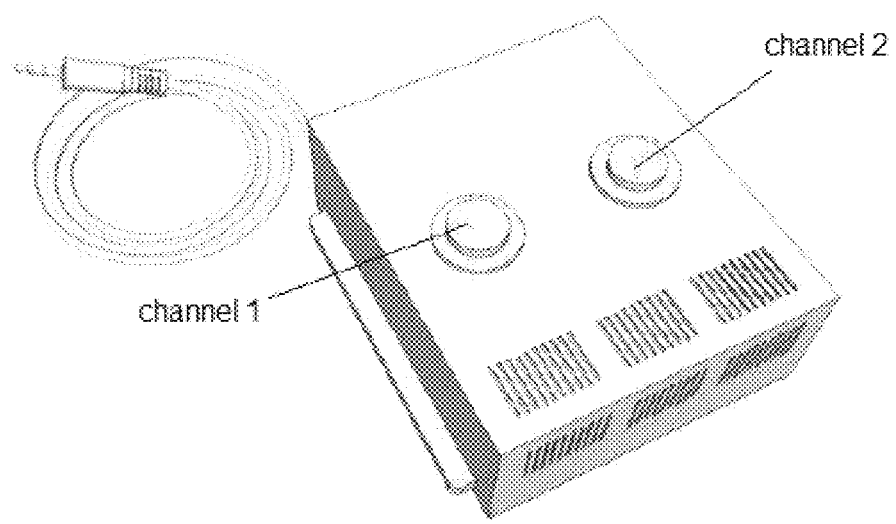
FIG. 3 shows the button unit for the device addressed by the invention.

FIG. 3 shows a preferred button unit fitted to the device addressed by the invention. Each button is a channel (channel 1, left button; channel 2, right button). Note the output cable with a two-channel connector (stereo). The preferred button unit is lightweight (under 0.5 kg), with large buttons that are well adapted to use by the hands and big toes. A broader variation of this button unit may be implemented for behavioral responses with the feet.

Figure 4:
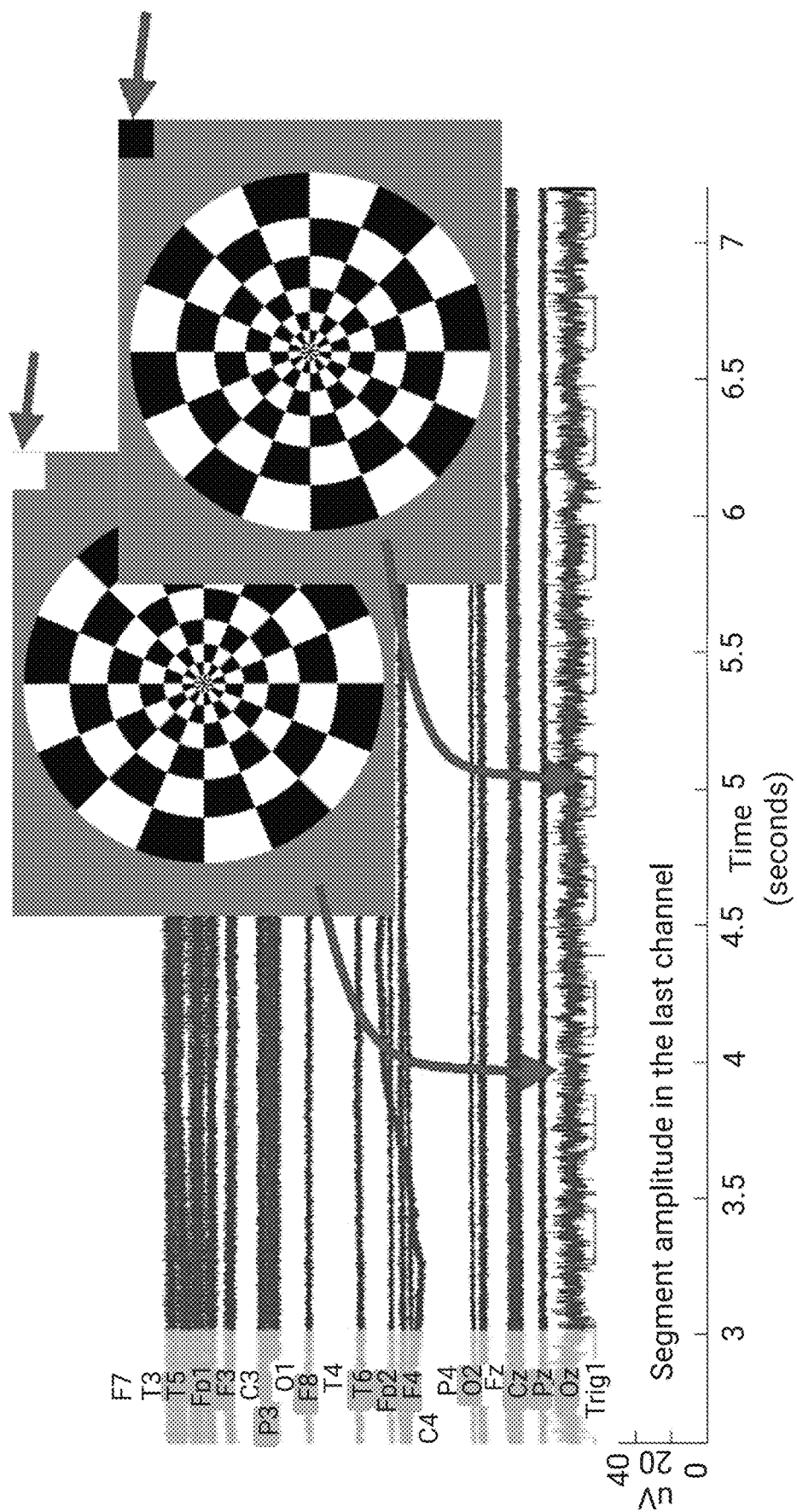
FIG. 4 conceptually demonstrates the function of the invention.

FIG. 4 presents an illustration of the functional paradigms of the device addressed by this invention, for a general understanding of the functioning of the device. Using any application (software) or even a media file played on a media player (such as audio files or video files in formats such as *avi or *mp4, as shown in this Figure), the stimulation pattern is presented to the subject whose evoked potentials are being evaluated. With the stimulation pattern, a small area along the edges alternate between white and black (presence and absence of light, indicated by the straight arrow) depending on light reversals in the target pattern fields, synchronizing the alternation of these patterns through the light detection module. On the electroencephalogram, the device constituting this invention "marks" the moment of each reversal (see the curved arrows), in order to allow studies of the evoked potentials in terms of the visual stimulation provided by this reversed pattern. The dotted line with the square waves represents the figure signal, sent from the device through the DC channel (through which the trigger signal from the light detection model enters the EEG equipment), overlaid on the electroencephalogram. The unbroken line is the EEG readings.

Figure 5A:
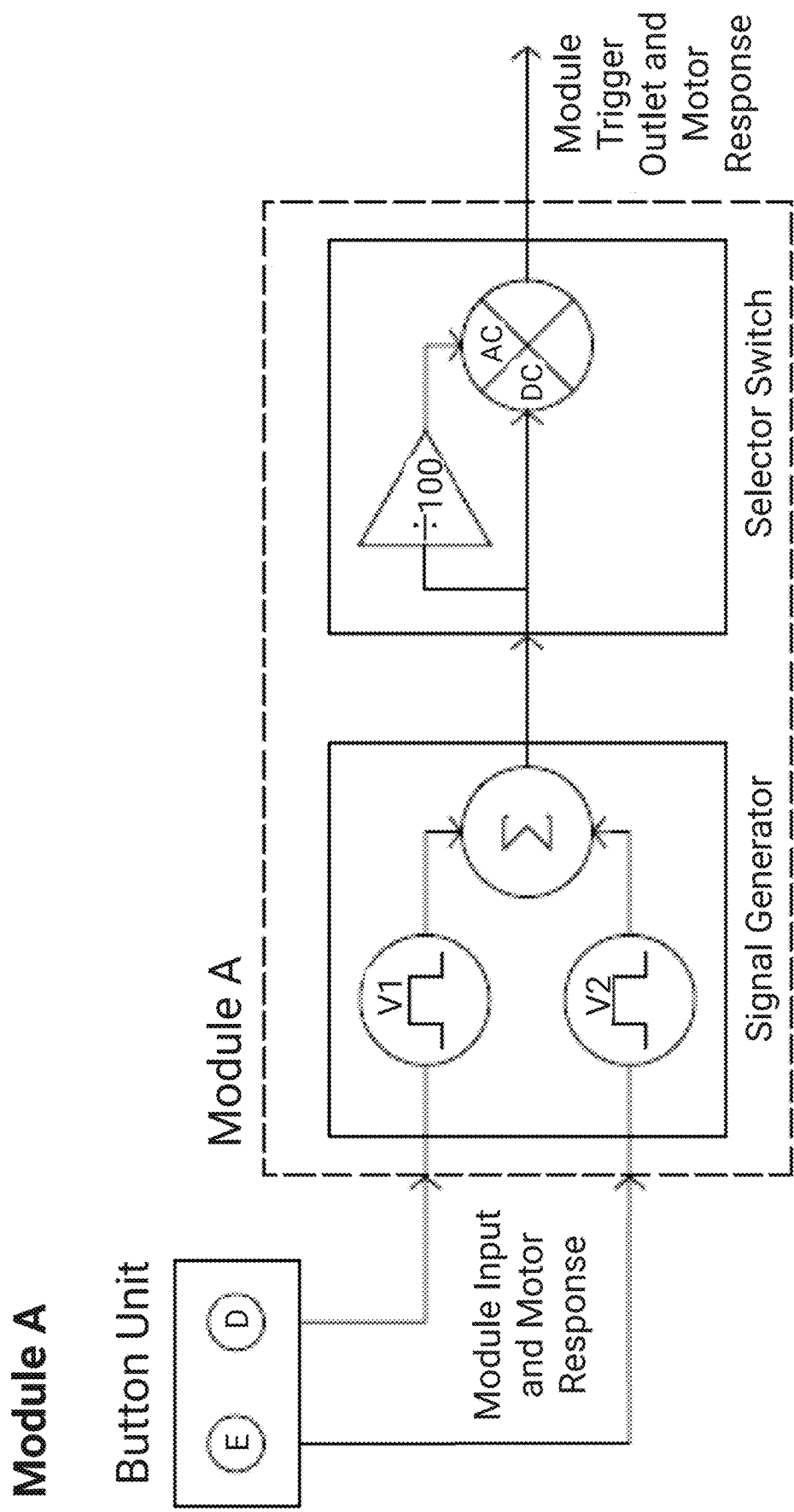
FIGS. 5A-5C are schematic drawings in concept blocks for a plurality of modules, according to various embodiments of the present disclosure.
Figure 5B:
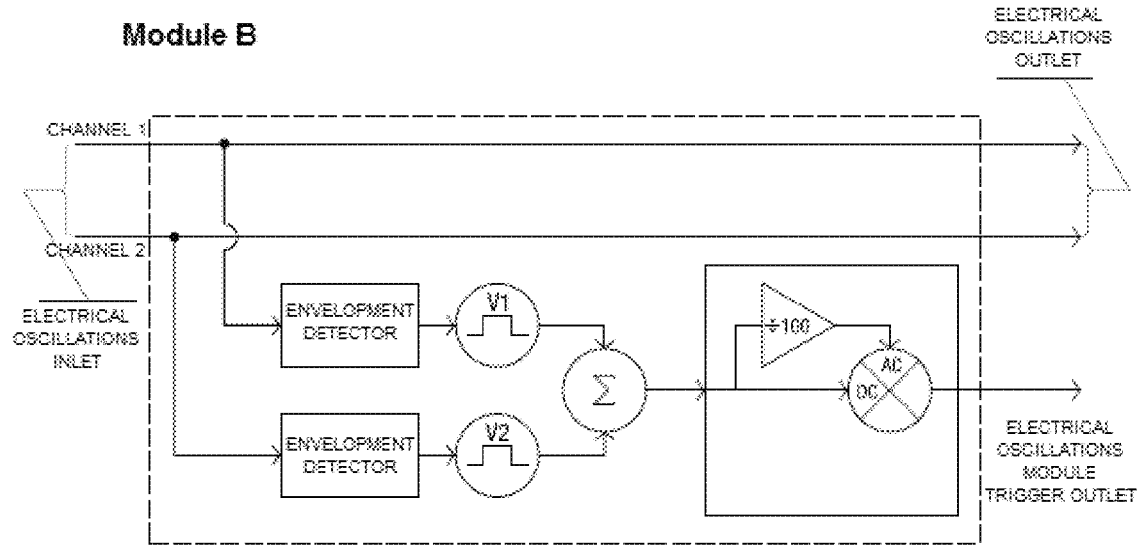
Figure 5C:
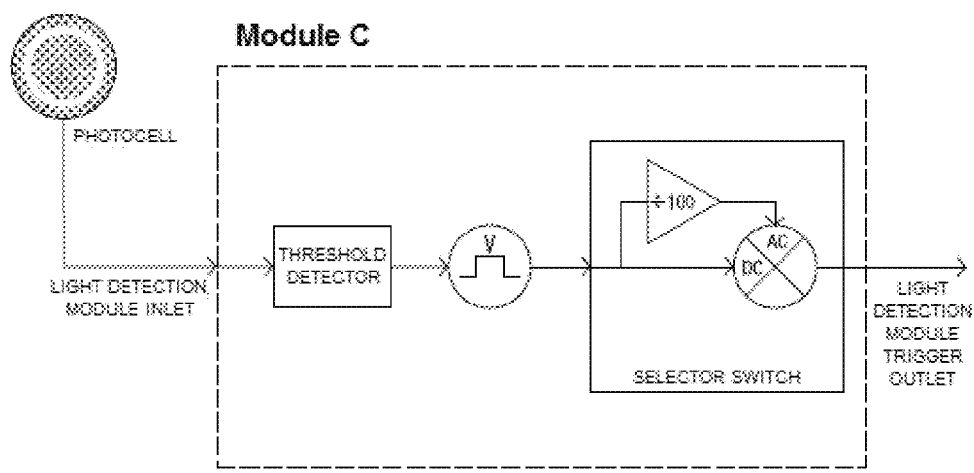

FIGS. 5A-5C present functional block diagrams according to various embodiments of this disclosure:

FIG. 5A illustrates the functioning of the motor response processing module. Pressing the right and/or left buttons on the button unit triggers the V1 and/or V2 voltage signal generator that, depending on the selector switch position, transmits in the form of square waves (with the same duration as the button is pressed) at voltages compatible with the DC or AC channels (÷100).

FIG. 5B illustrates the functioning of the electrical oscillation processing module. The electrical signals that enter through channel 1 and/or channel 2 runs through enveloping detector that generates a V1 and/or V2 voltage signal that, depending on the selector switch position, transmits in the form of square waves (with the same duration as the electrical oscillations in the input channels) at voltages compatible with the DC or AC channels (÷100). In parallel, there is a repeat system sending signals in channel 1 and 2 to an electrical oscillation output.

FIG. 5C illustrates the functioning of the light processing module. The electrical signal from the photocell runs through the threshold detector that generates a V1 voltage signal that, depending on the selector switch position, transmits in the form of square waves (with the same duration as the light signal activating the photocell) at voltages compatible with the DC or AC channels (÷100).

Figure 6:
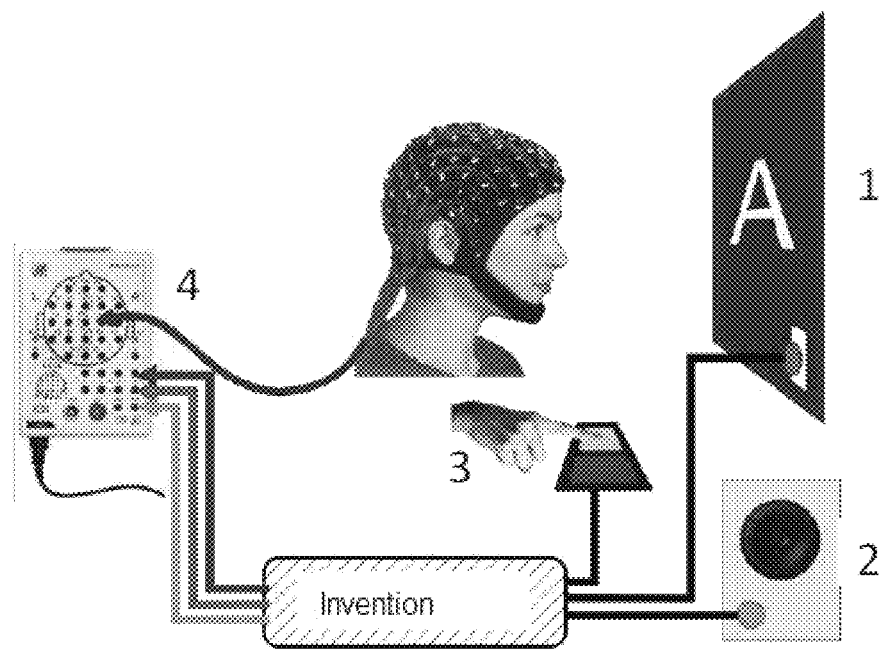
FIG. 6 is a representation of the modular device addressed by the invention.

FIG. 6 shows a representation with three modules of the modular device constituting the invention, in a preferred presentation, with one motor response processing module (3), one electrical oscillation processing module (2), and one light processing module (1). In the context of this Figure, we present a schematic diagram of the application of the device constituting the invention during the examination of a subject completing a test in which pictures are displayed (synchronized with the EEG [4] through the light processing module) and sounds (synchronized with the EEG through the electrical oscillation processing module), with the motor responses collected (and synchronized with the EEG) through the motor response processing module.

Consequently, so the device described here, it is possible to define and record markings taken directly from the presented stimuli and the responses generated by patients through only the electronic signal spread time.

Although the invention is described in details and refers to specific examples thereof, it will be clear to any specialist in this field that many changes and modifications may be made without moving away from its spirit and scope.

What is claimed is:

1. A modular device for analog electroencephalography synchronization with a plurality of events and motor behaviors, the modular device comprising:
a motor response processing module;
at least one of an electrical oscillation processing module or a light processing module; and
a power feed and control module in which a plurality of power switches a power input and a fuse are located, the power feed and control module being configured to distribute electricity to the motor response processing module and the at least one of the electrical oscillation processing module or the light processing module;
wherein the modular device is configured to:
receive a first analog signal associated with at least one physical stimulus to a subject, the first analog signal to be processed by the at least one of the electrical oscillation processing module or the light processing module;
receive a second analog signal relating to associated with a behavior type event of the subject, the second analog signal to be processed by the motor response processing module;
generate at least one output analog signal based on the first analog signal processed by the at least one of the electrical oscillation processing module or the light processing module; and
generate another analog signal based on the second analog signal processed by the motor response processing module.

2. The modular device of claim 1, wherein the modular device comprises the motor response processing module, the electrical oscillation processing module, and the light processing module.

3. The modular device of claim 1, wherein the motor response processing module comprises a device switch inlet with two mixed sub-channels that is configured to respond with square waves based on a selector switch position on a selector device in electrical connection with the motor response processing module.

4. The modular device of claim 3, wherein the motor response processing module produces a positive square wave of +2V, +3V, or +5V.

5. The modular device of claim 1, wherein the electrical oscillation processing module comprises an electrical oscillation inlet that is compatible with signals from a stereo audio output, an electrical oscillation module trigger outlet that detects 2, 3 or 5V waves, and an electrical oscillation outlet that reproduces a respective input signal, wherein the electrical oscillation processing module is configured to respond with square waves lasting as long as a duration of oscillation detected via the electrical oscillation inlet.

6. The modular device of claim 5, wherein the electrical oscillation inlet is configured to connect specific transducers (i) for physical events, the physical events being associated with at least one of temperatures, pressures or magnetic fields, and also (ii) for physiological events, the physiological events being associated with at least one of muscle activity, strength, skin conductance or ECG.

7. The modular device of claim 1, wherein the light processing module comprises a photocell inlet that is configured to detect light energy and respond with square waves corresponding to a duration of a light event corresponding to the detected light energy.

8. A method for analog synchronization of electroencephalography with a plurality of events and motor behaviors, the method comprising:
receiving information associated with physical light-type events, electrical oscillations and behavioral type motor responses from a subject;
generating a plurality of square wave trigger signals, each with a same duration as at least one of the physical light-type events, the electrical oscillations, or the behavioral type motor responses; and
transmitting the square wave trigger signals to a digital electroencephalogram apparatus through AC or DC channels;

wherein a first one of the plurality of the square wave trigger signals is based on the received information associated with at least one of the physical light-type events or the electrical oscillations, the at least one of the physical light-type events or the electrical oscillations corresponding to at least one physical stimulus presented to the subject, and a second one of the plurality of the square wave trigger signals is based on the received information associated with the behavioral type motor responses from the subject.

9. The method of claim 8, wherein the received information and the square wave trigger signals are respective analog signals .

10. The method of claim 8, wherein the first one of the plurality of square wave trigger signals and the second one of the plurality of square wave trigger signals are variable in amplitude, wherein the amplitudes are indicative of the at least one physical stimulus and/or behavioral type motor responses.

* * * * *

UNITED STATES PATENT AND TRADEMARK OFFICE
CERTIFICATE OF CORRECTION

PATENT NO. : 11,129,561 B2
APPLICATION NO. : 16/085775
DATED : September 28, 2021
INVENTOR(S) : Dimitri Marques Abramov et al.

It is certified that error appears in the above-identified patent and that said Letters Patent is hereby corrected as shown below:

In the Claims

In Column 8, Line 9, Claim 1, delete "signal relating to" and insert -- signal --.

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*